United States Patent [19]

Dempf et al.

[11] 4,220,607

[45] Sep. 2, 1980

[54] STABILIZED PERCHLOROETHYLENE

[75] Inventors: Dominik Dempf, Mehring-Oed; Rudolf Knabl, Burghausen; Ludwig Schmidhammer, Haiming, Marktl; Wilhelm Mack, Mehring, all of Fed. Rep. of Germany

[73] Assignee: Wacker-Chemie GmbH, Munich, Fed. Rep. of Germany

[21] Appl. No.: 19,388

[22] Filed: Mar. 12, 1979

[30] Foreign Application Priority Data

Mar. 17, 1978 [DE] Fed. Rep. of Germany ....... 2811779
Dec. 13, 1978 [DE] Fed. Rep. of Germany ....... 2853848

[51] Int. Cl.$^2$ ............................................. C07C 17/40
[52] U.S. Cl. ............................................. 260/652.5 R
[58] Field of Search ................................. 260/652.5 R

[56] References Cited

U.S. PATENT DOCUMENTS

| 3,133,885 | 5/1964 | Petering et al. | 260/652.5 R |
|---|---|---|---|
| 4,034,051 | 7/1977 | Dempf et al. | 260/652.5 |

Primary Examiner—C. Davis
Attorney, Agent, or Firm—Allison C. Collard; Thomas M. Galgano

[57] ABSTRACT

Stabilized perchloroethylene containing 0.001 to 0.1% by weight of N-alkylmorpholine, 0.001 to 0.01% by weight of alkylphenols, 0.0005 to 0.002% by weight of diisopropylamine, and 0.05 to 0.5% by weight of cyclohexeneoxide. By stabilization with the mixture of stabilizers, the perchloroethylene is stabilized to an extraordinary degree against attack by metals, particularly, decomposition through oxidation in contact with metals or metal salts, in some cases also upon exposure to light. A further improvement of the combined stabilizing action can be obtained by the addition of 0.005 to 0.1% by weight of epoxipropanol.

5 Claims, No Drawings

STABILIZED PERCHLOROETHYLENE

The present invention relates to stabilized perchloroethylene. Stabilized perchloroethylene is known per se. In German Offenlegungsschrift 24 49 667, an addition of N-alkylmorpholine and alkylphenol is suggested for the purpose of stabilization. From U.S. Pat. No. 3,133,885, it is known to add amines and oxiranes for purposes of stabilization. However, perchloroethylene stabilized according to the above Offenlegungsschrift, can no longer come up to today's technical specifications with regard to acid absorption; whereas, perchloroethylene stabilized according to U.S. Pat. No. 3,133,885, is unsatisfactory with regard to corrosion properties.

Finally, a stabilized perchloroethylene is known, which combines phenols and oxiranes with the possible addition of aniline or pyrrols. However, for stabilization against oxidation effects, both aniline and pyrrols must be used in comparatively large amounts.

It is the object of the present invention to provide stabilized perchloroethylene which is superior to hitherto stabilized perchloroethylene with regard to acid absorption capacity, corrosion stability and stabilization in general. According to the present invention, this object is achieved when stabilized perchloroethylene contains the following ingredients all in % by weight:

(a) 0.001 to 0.01% N-alkylmorpholine with straight or branched alkyl chains having 1–5 carbon atoms and, in some cases, aklyl substituents with 4 carbon atoms in the ring, and mixtures thereof;

(b) 0.001 to 0.01% alkylphenols with straight or branched alkyl chain, having 1–18 C atoms in o-and/or p-position, and mixtures thereof;

(c) 0.0005 to 0.002% diisopropylamine; and (d) 0.05 to 0.5% cyclohexeneoxide.

A preferred form of the stabilized perchloroethylene is characterized by the fact that n-alkylmorpholines, according to the instant invention, are present in amounts between 0.004 and 0.008%, the alkylphenols according to the instant invention, in amounts between 0.004 and 0.008%, and of the other two ingredients, according to the invention, diisopropylamine in amounts between 0.0008 and 0.0015%, and cyclohexeneoxide, in amounts of 0.1–0.3%. Frequently, it is advantageous to add epoxypropanol in amounts from 0.005–0.1%. Among the N-alkylmorpholines, the N-methyl or N-ethyl morpholines are especially advantageous; among the alkylphenols, the p-tert.-butylphenol.

It is surprising that it is possible to achieve a synergistically increased stabilization by the combination of known stabilizing components. This is all the more surprising, since it was known from the above-cited Offenlegungsschrift and from DRP 573 105, that the stabilizing action of alkylphenols and N-methylmorpholine is considerably decreased by the addition of diisopropylamine. By the simultaneous use of added cyclohexeneoxide, however, the stabilizing effect is not decreased, but, on the contrary, enhanced, particularly against corrosion attack. The effect is satisfactorily accomplished only by the addition of cyclohexeneoxide. By the addition of epoxypropanol, protection against the undesirable rearrangement of cyclohexeneoxide is thus obtained.

It is desirable that stabilized perchloroethylene having a lasting resistance to oxidizing decomposition in contact with metals, even if the amounts of stabilizing components are small. The stabilizing effect should also prevail against contact with alloys, metal salts, cutting oils, and the action of light and thermal exposure; furthermore, the perchloroethylene should have imparted thereto a long-lasting, increased acid absorption capability. Stability against metal attack by corrosion, should especially include iron, copper, zinc and aluminum.

The stabilizing components are contained in dissolved state in the perchloroethylene. As already mentioned, N-alkylmorpholine, according to the instant invention, may have straight or branched alkyl chains with 1–5 C-atoms; furthermore, the ring may contain substituents in 2-,3-,5-, or 6-position with alkyl chains up to 4 C-atoms. The preferred compounds are N-methyl- and N-ethylmorpholines. The alkylphenols may be o- and/or p-alkylphenols, having 1–18 C-atoms with straight or branched alkyl chains. Preferred are alkylphenols having 2–8 C-atoms in the alkyl chain, more particularly, such alkylphenols having a branched chain with 3–5 C-atoms in p-position. The alkylphenols may also be used in mixtures.

Particularly good stabilizations are obtained with a mixture of N-methylmorpholine, p-tert.-butylphenol, diisopropylamine and cyclohexeneoxide. The effectiveness as stabilizer against oxidative effect is found by tests corresponding to the conditions of the MIL-test 7003. In the test, 200 ml perchloroethylene are heated and exposed in a test flask to light from below by a frosted 150 Watt bulb. The perchloroethylene is brought to boiling and gets into contact with a steel strip of 12 mm $\times$ 50.8 mm $\times$ 1.59 mm, which is suspended by means of a VA-wire in a reflux cooler placed on top of the flask. A second steel strip of 6.35 mm $\times$ 19.5 mm $\times$ 1.59 mm is placed in the boiling liquid at the flask bottom. Through a glass tube having a diameter of 3 mm, which ends 6.35 mm above the flask bottom, an oxygen stream saturated with water is passed into the perchloroethylene at 10 to 12 bubbles per minute. The flask contents are cooled and a specimen is withdrawn therefrom. The acidity in an aqueous extract of the same, is determined by titration with 0.1 N sodium hydroxide solution, with phenolphtalein as indicator. Specimens which have an acidity content of more than 0.02% by weight of HCl, after the 48-hour test, are ineffectively stabilized. The measure for the stabilizing effect is the time it takes to reach the acidity limit of 0.02% by weight in perchloroethylene, expressed in hours.

The acid-absorbing capacity of stabilized perchloroethylene is determined as follows: 25 cc of hydrochlorinating solution (made from 1 cc conc.hydrochloric acid and 250 cc methanol,) are filled in an Erlenmayer flask with 25 cc of distilled water and titrated with 0.1 N sodium hydroxide solution with phenolphtalein as indicator, until a lasting ink color is obtained. (Consumption A in ml.) Then, 25 cc of the hydrochlorination reagent and 15 cc of the specimen are pipetted into a flask and refluxed for 5 minutes. After cooling, 25 cc of distilled water are added and titration takes place with 0.1 N sodium hydroxide solution. (Consumption B in ml.) The acid absorption capacity is calculated as $$\frac{(A - B) \times 0.4}{V \times D} = \text{weight \% sodium hydroxide-solution}$$

V—Volume of the specimen in cc
D—Density of the specimen in g/cc

The stabilizer effectiveness against corrosion is demonstrated by simple tests, wherein metal strips of iron, copper, aluminum or zinc, which are partly immersed in the liquid, are refluxed with perchloroethylene for 168 hours. The extent of discoloration or the tar formation on the surface of the metal is a measure of the corrosive properties of the stabilized perchloroethylene.

The Examples are listed in TABLE I, which follows, except for Example 10 which is described in detail.

TABLE I

| Example Number | Stabilizer in ppm | Hours Until Acidity Limit Is Reached | Acid Absorption Capacity After 72 Hours, % NaOH Subsequently Refluxed 10 Times | Corrosion Reaction To Fe, Cu, Zn & Al |
|---|---|---|---|---|
| 1 | 15 Diisopropylamine<br>50 N-Methylmorpholine<br>30 p.-tert.-Butylphenol | 100 | 0,01 | Strong Corrosion Cu, Zn |
| 2 | 50 N-Methylmorpholine<br>30 p.-tert.-Butylphenol | 145 | 0,01 | Slight Corrosion Fe, Cu, Zn |
| 3 | 50 N-Methylmorpholine<br>30 p.-tert.-Butylphenol<br>2,500 Cyclohexeneoxide | 180 | 0,06 | Corrosion Fe, Zn |
| 4 | 15 Diisopropylamine<br>30 p.-tert.-Butylphenol<br>2,500 Cyclohexeneoxide | 70 | 0,06 | Slight Corrosion By Fe, Cu, Al |
| 5 | 15 Diisopropylamine<br>50 N-Methylmorpholine<br>30 p.-tert.-Butylphenol<br>2,500 Cyclohexeneoxide | 390 | 0,07 | No Corrosion By Fe, Cu, Al, Zn |
| 6 | 15 Diisopropylamine<br>50 N-Methylmorpholine<br>30 p.-tert.-Butylphenol<br>2,500 Propyleneoxide | 175 | 0,04 | Slight Corrosion By Fe, Zn, Cu |
| 7 | 15 Diisopropylamine<br>50 N-Methylmorpholine<br>30 p.-tert.-Butylphenol<br>2,500 Butyleneoxide | 180 | 0,05 | Corrosion By Fe, Cu, Zn |
| 8 | 15 Diisopropylamine<br>30 N-Methylmorpholine<br>30 p.-tert.-Butylphenol<br>2,500 Epichlorhydrine | 190 | 0,06 | Slight Corrosion By Fe, Zn |
| 9 | 15 Aniline<br>50 N-Methylmorpholine<br>30 p.-tert.-Butylphenol<br>2,500 Cyclohexeneoxide | 170 | 0,06 | Strong Corrosion By Cu, Fe, Zn |

EXAMPLE 10

Addition of epoxipropanol.

Perchloroethylene was stabilized by 50 ppm N-methylmorpholine, 15 ppm diisopropylamine, 50 ppm p.-tert.-Butylphenol, 2,500 ppm cyclohexeneoxide and 200 ppm epoxipropanol.

Then, in a first test, 200 ppm, and in a second test, 400 ppm zinc chloride, were added; and subsequently, to heating, boiling was carried out for 72 hours. After this time, the cyclohexeneoxide present was unchanged. In the gas chromatogram, 2,460 ppm cyclohexeneoxide were found, cyclopentylaldehyde was not observed in traces, and the mixture did not have any unusual smell.

It will be obvious to those skilled in the art that other changes and variations can be made in carrying out the present invention, without departing from the spirit and scope thereof, as defined in the appended claims.

What is claimed is:

1. Stabilized perchloroethylene, containing
   (a) 0.001 to 0.01% by weight N-alkylmorpholine with straight- or branched-chain alkyl chains having 1–5 carbon atoms, and mixtures thereof;
   (b) 0.001 to 0.01% by weight alkylphenols with straight- or branched-chains, the alkyl chains having 1–18 carbon atoms in o- or p-positions, or both, and mixtures thereof;
   (c) 0.0005 to 0.002% by weight of diisopropylamine; and
   (d) 0.05 to 0.5% by weight of cyclohexeneoxide.

2. The stabilized perchloroethylene according to claim 1 wherein the N-alkylmorpholine mentioned under step (a) also is substituted in the ring with alkyl chains up to 4 carbon atoms.

3. The stabilized perchloroethylene according to claim 1 wherein the amount of N-alkylmorpholine is 0.004 to 0.008% by weight, the amount of alkylphenols 0.004 to 0.008% by weight, the amount of diisopropylamine 0.0008 to 0.0015% by weight, and the amount of cyclohexeneoxide is 0.1 to 0.3% by weight.

4. The stabilized perchloroethylene according to claim 1 wherein the N-alkylmorpholine is methyl- or ethylmorpholine, and the alkylphenol is p.-tert.-Butylphenol.

5. The stabilized perchloroethylene according to claim 1 also containing 0.005 to 0.1% by weight of epoxipropanol.

* * * * *